United States Patent
Narayana (10) Patent No.: US 8,834,917 B2
(45) Date of Patent: Sep. 16, 2014

(54) NANOPARTICLE COMPOSITION AND PROCESS THEREOF

(75) Inventor: Chandrabhas Narayana, Karnataka (IN)

(73) Assignee: Jawaharlal Nehru Centre for Advanced Scientific Research (IN)

( * ) Notice: Subject to any disclaimer, the term of this patent is extended or adjusted under 35 U.S.C. 154(b) by 226 days.

(21) Appl. No.: 12/739,395

(22) PCT Filed: Nov. 14, 2008

(86) PCT No.: PCT/IN2008/000771
§ 371 (c)(1),
(2), (4) Date: Apr. 22, 2010

(87) PCT Pub. No.: WO2009/063508
PCT Pub. Date: May 22, 2009

(65) Prior Publication Data
US 2010/0233245 A1    Sep. 16, 2010

(30) Foreign Application Priority Data
Nov. 13, 2007   (IN) .................... 02628/CHE/2007

(51) Int. Cl.
*A61K 9/70*    (2006.01)
*A61K 33/38*   (2006.01)
*A01N 59/16*   (2006.01)

(52) U.S. Cl.
CPC . *A61K 9/70* (2013.01); *A01N 59/16* (2013.01); *A61K 2800/413* (2013.01)

USPC .......................................... 424/443; 424/618

(58) Field of Classification Search
None
See application file for complete search history.

(56) References Cited

U.S. PATENT DOCUMENTS

2005/0182152 A1*  8/2005  Nonninger et al. ........... 523/122
2007/0292469 A1* 12/2007  Rothenburger et al. ...... 424/423

FOREIGN PATENT DOCUMENTS

WO    WO 03/063996         8/2003
WO    WO 03063996 A2  *    8/2003

OTHER PUBLICATIONS

Koslow (WO 03/063996 A2 published on Aug. 7, 2003; reference B1 on IDS dated Apr. 22, 2010).*
"Embed", Merriam-Webster Dictionary, accessed May 7, 2012, available at http://www.merriam-webster.com/dictionary/embed.*
PCT International Search Report, PCT/IN2008/000771, May 14, 2009, 2 Pages.
PCT International Preliminary Examination Report, PCT Application No. PCT/IN2008/000771, Feb. 25, 2010, three pages.

\* cited by examiner

*Primary Examiner* — H. Sarah Park
(74) *Attorney, Agent, or Firm* — Fenwick & West LLP (57) ABSTRACT

The present invention relates to nanoparticle composition comprising cellulose nanofibers embedded with nanosized material. More particularly the present invention relates to cellulose nanofibers embedded with silver or iron oxide embedded silver. In addition the present invention is also related to the preparation of the cellulose nanofibers embedded with nanosized material. The nanoparticle composition is antibacterial in nature and can be utilized in various antibacterial applications.

6 Claims, 8 Drawing Sheets

NANOPARTICLE COMPOSITION AND PROCESS THEREOF

FIELD OF INVENTION

The present invention relates to nanoparticle composition comprising cellulose nanofibers embedded with nanosized material. More particularly the present invention relates to cellulose nanofibers embedded with silver or iron oxide embedded silver. In addition the present invention is also related to the preparation of the cellulose nanofibers embedded with nanosized material.

BACKGROUND OF THE INVENTION AND PRIOR ART

Nanoparticles of silver, MgO, ZnO, $Fe_3O_4$, ZnS, CuO and $SnO_2$ have assumed great importance in view of their application in biomedical and bio technology, pollution abatement, biosensor technology and as agents of antimicrobial therapy. Several ways and means have been pioneered in the recent past, particularly, towards the production of nanoparticles of various metals individually and in combination. Nanosilver is fascinating owing to its antimicrobial activity useful in the process of reducing microbial contamination in the field of food processing and hygiene control. In the production of nanoparticles use of less toxic or non-toxic chemicals has always been preferred in the form of reducing agents and stabilizers as chemically green procedures are preferred over conventional synthesis.

Microorganisms cause mild to severe infections in human beings, animals and plants. Among the inorganic antimicrobial agents silver is a well known broad-spectrum agent employed most extensively since ancient times to fight infections caused by bacteria, yeast, fungi as well as virus. Nanosilver is known to inhibit or inactivate microorganisms effectively with lower toxicity to tissue. Due to the large surface area and high reactivity nanosilver is endowed with remarkable antimicrobial property. Because of long lasting biocidalaction nanosilver preparations are currently being used as antimicrobial agents in several industries such as ceramics, paper, plastic and packing films.

Cellulose is a biopolymer mostly produced by plants and micro-organisms, however some marine animals were also shown to produce cellulose. Though wood is the major source of plant cellulose its separation and purification is a tedious process with the intervention of toxic chemical, hence, its large-scale application in pure form is impracticable. Bacterial cellulose produced by *Acetobacter xylinum* (*Gluconacetobacter xylinus*) is an attractive biomaterial with its intrinsic nanostructural hierarchy, its purity, mechanical strength and chemical robustness. This bacterium produces extracellular cellulose under static culture condition in the form of highly reticulated net like structure along with the entrapped bacteria, media components and protein. The whole complex is referred to as pellicle. The cellulose is purified using alkali treatment at boiling temperature. In the present investigation we have attempted to develop a novel antimicrobial composite material comprising of bacterial cellulose and nanosilver. Several researchers have reported the use of plant cellulose in the preparation of antibacterial silver formulations. We report the preparation of silver nanoparticles embedded into nanoparticulate bacterial cellulose as stabilizer for effective inhibition of Staphylococcus aureus. The process is simple and scalable for its real-time applications in various fields such as food packaging and in antimicrobial therapy.

OBJECTS OF THE INVENTION

The principal object of the present invention is to develop nanoparticle composition comprising cellulose nanofibers embedded with nanosized material.

Yet another object of the present invention is to develop a method of preparation of nanoparticle composition comprising cellulose nanofibers embedded with nanosized material.

Yet another object of the present invention is to use the composition comprising cellulose nanofibers embedded with nanosized material in the manufacture of antibacterial medicament.

STATEMENT OF INVENTION

Accordingly, the present invention provides a nanoparticle composition comprising cellulose nanofibers embedded with nanosized material; a method of preparation of nanoparticle composition comprising cellulose nanofibers embedded with nanosized material, said method comprising steps of: mixing metal salt solution with cellulose nanofibers and adding reducing agent to the mixture to reduce the silver salt to obtain said nanoparticles composition wherein the nanosized material is metal; a method of preparation of nanoparticle composition comprising cellulose nanofibers embedded with nanosized material wherein the nanosized material is iron oxide embedded metal, said method comprising steps of adding metal salt solution to a mixture of cellulose nanofibers and iron oxide, reducing metal salt using reducing agent, separating the silver embedded iron oxide on cellulose nanofibers, washing with water followed by drying to obtain said nanoparticles composition and a method of preparation of nanoparticles composition comprising cellulose nanofibers embedded with nanosized material wherein the cellulose fibers is in paper form and the nanosized material is metal, said method comprising steps of: soaking cellulose papers in metal salt solution, washing the soaked cellulose paper, soaking the washed cellulose papers in solution of reducing agent, washing the cellulose papers and drying to obtain said nanoparticles composition.

DETAILED DESCRIPTION OF INVENTION

The present invention is in relation to nanoparticle composition comprising cellulose nanofibers embedded with nanosized material.

In another embodiment of the invention, the cellulose fibers are in the form of paper.

In yet another embodiment of the invention, the nanosized material is selected from a group comprising metal and iron oxide embedded metal.

In still another embodiment of the present invention, the metal is silver.

In still another embodiment of the present invention, the iron oxide is selected from a group comprising $Fe_3O_4$, γ-$Fe_2O_3$, preferably $Fe_3O_4$.

In still another embodiment of the present invention, the silver is sourced from a group comprising silver nitrate, silver chloride, silver carbonate, preferably silver nitrate or any combination thereof.

In still another embodiment of the present invention, the nanoparticles composition is antibacterial in nature.

The present invention is also in relation to a method of preparation of nanoparticle composition comprising cellulose nanofibers embedded with nanosized material, said method comprising steps of:
 a) Mixing metal salt solution with cellulose nanofibers; and
 b) adding reducing agent to the mixture to reduce the metal salt to obtain said nanoparticles composition.

In another embodiment of the invention, the nanosized material is a metal.

In yet another embodiment of the invention, the metal salt solution and cellulose nanofibers are mixed by sonication for about 30 min.

The present invention is also in relation to a method of preparation of nanoparticle composition comprising cellulose nanofibers embedded with nanosized material, said method comprising steps of:
 a) adding metal salt solution to a mixture of cellulose nanofibers and iron oxide;
 b) reducing metal salt using reducing agent;
 c) separating the silver embedded iron oxide on cellulose nanofibers; and
 d) washing with water followed by drying to obtain said nanoparticles composition.

In another embodiment of the invention, the nanosized material is iron oxide embedded metal In still another embodiment of the invention, the silver embedded iron oxide on cellulose nanofibers are separated by magnetic separation.

The present invention is also in relation to a method of preparation of nanoparticles composition comprising cellulose nanofibers embedded with nanosized material, said method comprising steps of:
 a) soaking cellulose papers in metal salt solution;
 b) washing the soaked cellulose paper;
 c) soaking the washed cellulose papers in solution of reducing agent;
 d) washing the cellulose papers of step c; and
 e) drying to obtain said nanoparticles composition.

In another embodiment of the invention, the cellulose fiber is in the paper form.

In yet another embodiment of the present invention, the nanosized material is a metal.

In still another embodiment of the present invention, the cellulose papers are soaked in metal salt solution for about 30 min.

In still another embodiment of the present invention, the metal salt solution is about 1 mM solution in concentration.

In still another embodiment of the present invention, the cellulose papers are washed with mixture ethanol and water, wherein the concentration of ethanol ranges from about 75% to about 85%

In still another embodiment of the present invention, the reducing agent is selected from a group comprising hydrazanium hydroxide and sodium borohydride.

In still another embodiment of the present invention, the drying is carried out at a temperature ranging from about 20° C. to a temperature of about 30° C. preferably 25° C.

In still another embodiment of the present invention, the metal is silver.

In still another embodiment of the present invention, the metal salt is selected from a group comprising silver nitrate, silver chloride, silver carbonate preferably silver nitrate or combination thereof.

In still another embodiment of the present invention, the metal salt solution is prepared by dissolving metal salt in water.

In still another embodiment of the present invention, the reducing agent is added dropwise with constant stirring to the mixture.

In still another embodiment of the present invention, the reducing agent is selected from a group comprising hydrazanium hydroxide, sodium borohydride, hydroxyl ammonium hydrochloride and tri-sodium citrate, preferably hydrazanium hydroxide.

In still another embodiment of the present invention, the preparation of nanoparticle composition is carried out at a temperature ranging from about 20° C. to a temperature of about 30° C. preferably 25° C., when the reducing agent is hydrazanium hydroxide.

In still another embodiment of the present invention, the preparation of nanoparticle composition is carried out at a temperature ranging from about 20° C. to a temperature of about 30° C. preferably 25° C., when the reducing agent is sodium borohydride.

In still another embodiment of the present invention, the preparation of nanoparticle composition is carried out at a temperature ranging from about 20° C. to a temperature of about 30° C. preferably 25° C., when the reducing agent is tri-sodium citrate.

In still another embodiment of the present invention, the preparation of nanoparticle composition is carried out at a temperature ranging from about 20° C. to a temperature of about 30° C. preferably 25° C., when the reducing agent is hydroxyl ammonium hydrochloride.

In still another embodiment of the present invention, the preparation of nanoparticle composition is carried out by maintaining about 1 mM alkalinity by adding sodium hydroxide solution when the reducing agent is hydroxyl ammonium hydrochloride.

The present invention is also in relation to the use of nanoparticle composition comprising cellulose nanofibers embedded with nanosized material in the manufacture of antibacterial medicament.

In another embodiment of the present invention, the medicament is used in food packaging, clothing, medical applications, face masks, laundry detergent and air filters. In yet another embodiment of the present invention, the medical applications is selected from a group comprising wound coverings, dressings, bandages, biological implants, and diagnostic biomedical optical imaging.

In still another embodiment of the present invention, the nanoparticle composition is non-toxic and free from side effects.

Antimicrobial activity of nanosilver is very broad against various microorganisms and it is of great significance because of its ability to inhibit the growth or inactivate microorganisms such as fungi, algae, bacteria, yeast and virus. In this paper we report the synthesis and anti-bacterial activity of nanosilver stabilized with bacterial nanocellulose matrix. UV-visible absorption spectroscopy, energy dispersive X-ray spectroscopy (EDAX), Transmission electron microscopy (TEM) and Field emission-scanning electron microscopy (FE-SEM) were used to characterize the composite. The composite material had shown remarkable stability without aggregation of silver nanoparticles with the nanocellulose functioning as capping agent conformed using the FE-SEM. The antibacterial activity of the nanocomposite was assessed against *Staphyloccus aureus*. The nanocomposite obtained through the use of hydrazine showed optimum growth inhibition against *Staphyloccus aureus* the ones prepared using sodium borohydride as reducing agent. The NaOH treated nanocellulose showed further enhancement in the antibacterial activity of the nanocomposite, which is rather attributed to its higher swelling characteristic, and retention of hydrogel property. It was also noticed that these composites not only inhibit the bacterial growth but also works as bactericidal at very low concentration of silver (110 µg ml$^{-1}$). Due to its high antibacterial activity, and stabilizing effect of bacterial cellulose matrix, the nanocomposite appears to be promising for its application in biomedical technology, in antimicrobial textile and in food processing industry.

On addition of silver nitrate to the aqueous cellulose fiber, the fibers are randomly distributed and swelled. Due to the presence of large number of terminal hydrophilic hydroxyl —OH groups on the membrane of the cellulose fibers, Ag$^+$ ions get easily deposited on the membrane and subsequently they can be reduced. The reduction of Ag$^+$ in the cellulose silver nitrate aqueous mixture was performed by using a set of reducing agents as illustrated in Table 1.

The use of water as a solvent in the synthesis of silver nanoparticles causes an immediate agglomeration due to the high polarity of water. In the synthesis of nanoparticles stabilizers such as polyvinylpyrrolidone (PVP), ethylene glycol, various other biopolymers and citrate have been reported. In the present study we employed bacterial cellulose in the form of a nanoparticulate gel. The cellulose was found to protect the nanosilver formed from aggregation or coalescence by steric hindrance. To optimize the concentration as well as the size of the silver nanoparticles, the concentration of Ag$^+$ was kept at 1 mM, since higher concentration results in comparatively larger particles with lower antimicrobial efficacy. We have tested that the inhibition is due to the silver nanoparticles and not because of the presence of residual chemicals such as the by-products of reducing agents. In addition, high concentrations of silver would render toxicity to animal cells. High concentration of silver may also favor aggregation. The pH, which is also a paramount controlling parameter of the nanoparticles size as well as the antibacterial activity, is monitored and listed in Table 1. The synthesized cellulose nanocomposites were found to be stable at least over a period of 3 months in aqueous form at room temperature with no indication of aggregation or discoloration and with no detectable loss of silver nano particles.

Figure 1:
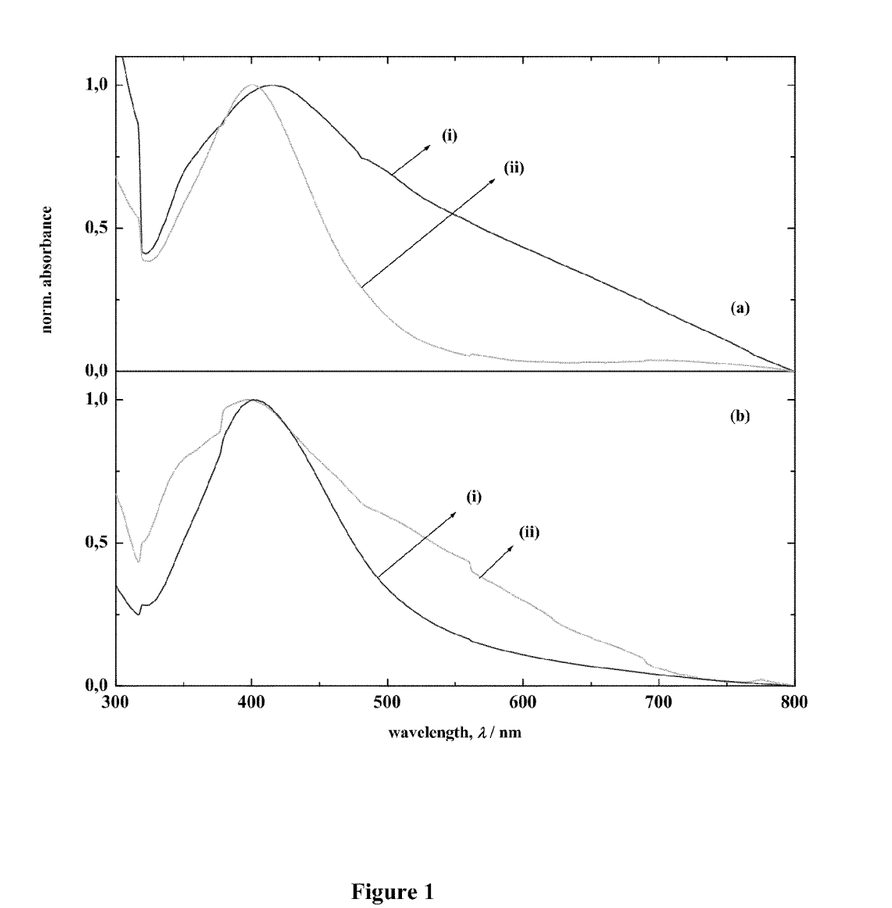
FIG. 1: UV-visible absorption spectra of silver loaded cellulose nanocomposites obtained via reduction of silver nitrate by using (i) hydrazine and (ii) sodium borohydride for (a) untreated and (b) NaOH treated cellulose fibers, respectively.
Figure 2:
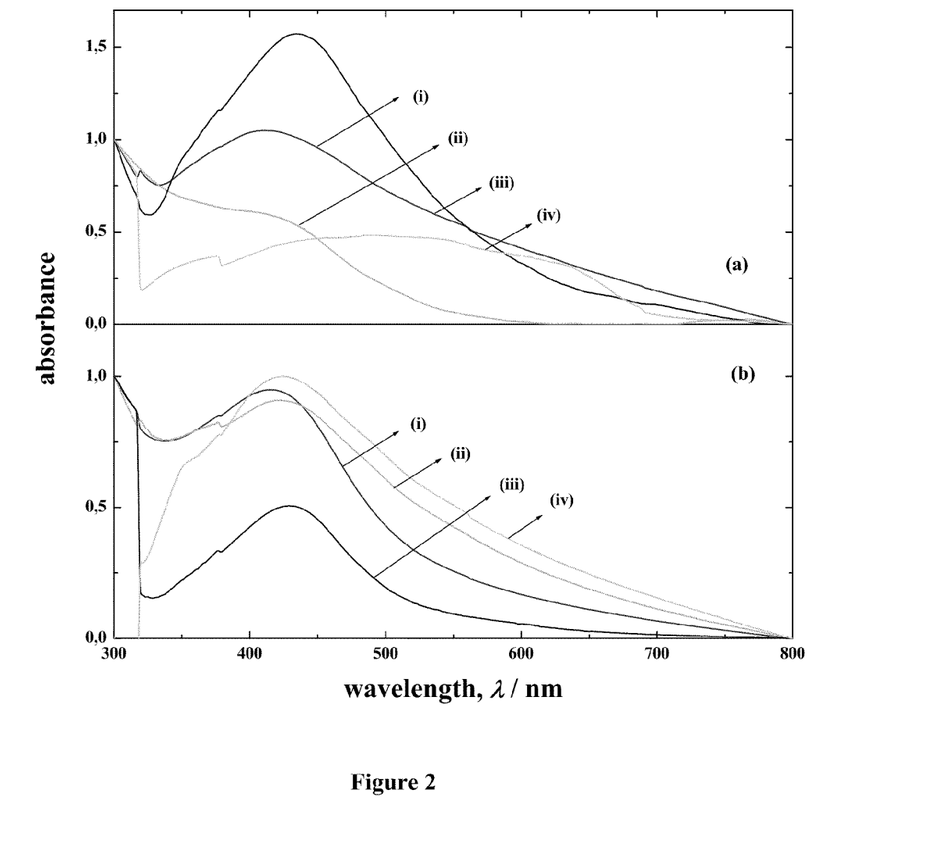
FIG. 2: UV-visible absorption spectra of silver loaded cellulose nanocomposites obtained via reduction of silver nitrate by using (i) glucose, (ii) ethylene glycol, (iii) tri-sodium citrate and (iv) hydroxylammonium hydrochloride for (a) untreated and (b) NaOH treated cellulose fibers, respectively.

The formation of Ag nanoparticles was confirmed by UV-visible absorption spectra and Fe-SEM imaging. FIG. 1 shows the UV-visible absorption spectrum of the silver loaded cellulose nanocomposite obtained by using hydrazine and sodium borohydride and the corresponding spectrum for the remaining reducing agents; glucose, ethylene glycol, trisodium citrate and hydroxyl ammonium hydrochloride are shown in FIG. 2. The bare cellulose does not show any absorption in the UV-visible region and the silver loaded composite shows a strong absorption in the UV-visible region due to surface plasmon resonance (SPR) of silver nanoparticles. The collective oscillation of free electrons in metallic nanoparticles known as SPR appears in the UV-visible region. The position and broadening of SPR depends on the shape, size, and stabilizing agent and on the dielectric constant of the medium. The absorption maximum of SPR observed is illustrated in Table 1. The observed SPR is red shifted in comparison to their corresponding sol (citrate or borohydride reduced sol) and is attributed to dipole resonance interactions between nanoparticles, a well known phenomena in noble metal nanoparticles.

Figure 3:
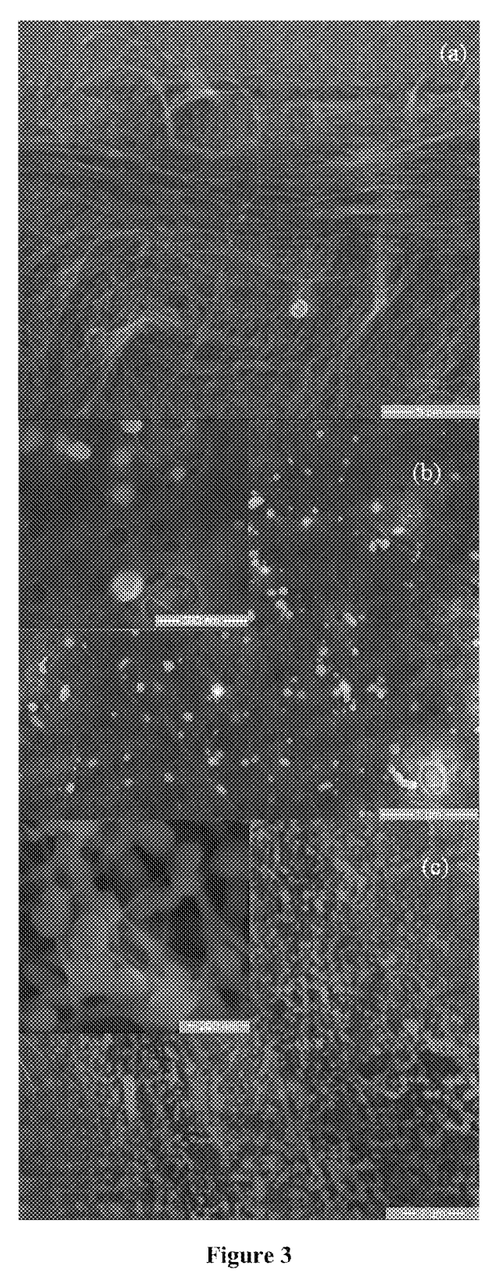
FIG. 3: FE-SEM images of cellulose fibers (a) and silver loaded cellulose fiber nanocomposite obtained via reduction of silver nitrate by using (b) hydrazine and (c) sodium borohydride, respectively. The insets show the images at higher magnifications.

FIGS. 3*a*, *b* and *c* show the FE-SEM images of the cellulose fibers and silver loaded fibers obtained by using hydrazine and sodium borohydride, respectively. The mean diameter of the particles is roughly 82±34 and 100±14 nm for hydrazine and sodium borohydride reduced nanocomposite, respectively. The image display uniform network structure with the silver nanoparticles is observed to be distributed homogeneously on the cellulose surfaces as individual, non-aggregated particles. The images reveal that the particles are strongly adhered to the cellulose fibers. This adherence helps in stabilizing and in immobilizing the silver nanoparticles and thus preventing from agglomeration. The surface functional groups of cellulose fiber are the reason for the strong interaction of silver nanoparticles. This is one of the major advantages of the present protocol where other foreign chemicals, surfactant or polymer are not necessary to stabilize silver nanoparticles. The images also reveal that the cellulose fibers are not damaged during the synthesis.

After obtaining the robust nanostructures their practical application in bacterial inhibition is examined. The antibacterial activity of nanosilver is mainly attributed to its affinity towards biologically important functional groups such as sulfhydryl amino, imidazole, carboxyl and phosphate groups, which exist mainly in protein such as enzymes. Nanosilver is also known to interact with DNA resulting in the formation of pyramidine dimers preventing its replication.

Figure 4:
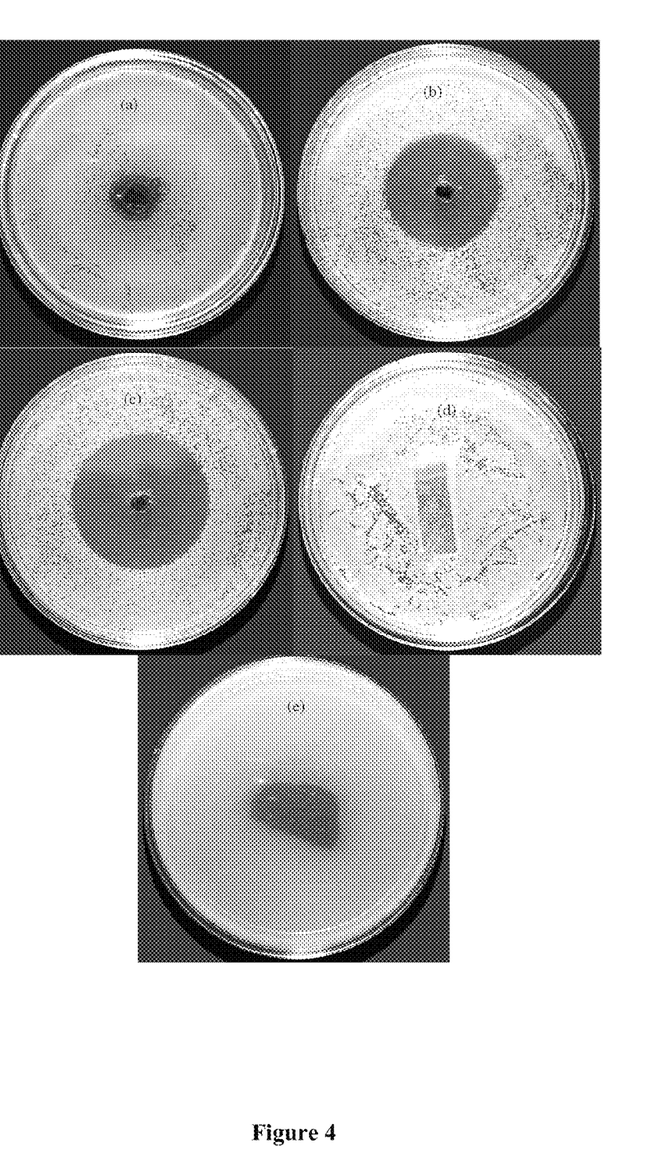
FIG. 4: Antibacterial efficacy of (a) sodium borohydride reduced, (b) hydrazine reduced and (c) hydrazine reduced and NaOH treated silver loaded cellulose fiber nanocomposite and of (d) sodium borohydride reduced and (e) hydrazine reduced cellulose paper silver nanocomposite, respectively.
Figure 5:
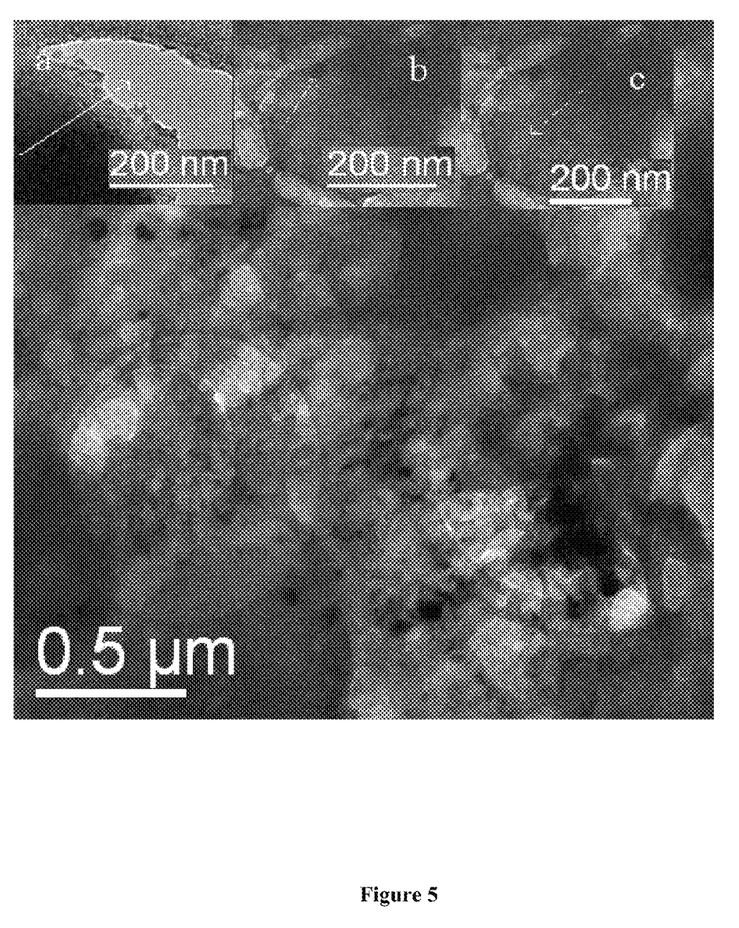
FIG. 5: TEM image of effected bacterial cell by cellulose Ag nanocomposite. The insets (a) shows the detaching of the outer membrane from inner cytoplasmic membrane by Ag nps, (b) shows the penetration of Ag nps inside the bacterial cell and (c) shows electron light region in bacterial cell.

The antibacterial activity of nanocomposite was considerably higher against the indicator pathogen *Staphylococcus aureus* as evidenced by the inhibitory zone (FIG. 4). The inhibition zone was around 2.6 cm radius in tryptic soya agar in the presence of NaOH treated cellulose. The nanocomposites prepared using non-swollen (no alkali treatment involved) was comparatively less inhibitory (2.0 cm radius). In addition the antibacterial effect of silver nanocomposite on stationary phase cells of *Staphylococcus aureus* was investigated using TEM (FIG. 5). Further the nanocomposite was shown to lyse the bacterial cells of stationary phase by way of perturbing the bacterial cell wall and consequent entry into the cell protoplasm causing leakage of cell contents and plasmolysis as seen in the TEM images (FIG. 5). The amount of silver in 50 µl composite was calculated to be around 5.4 µg, which is considerably low and more over a remarkable inhibitory zone was shown in the study in comparison to the earlier investigations. We report the biocidal effect of silver nanoparticles during growth and after cessation of growth of the pathogen. It was also found that washing of nano composite with distilled water deprive of its antibacterial activity to a great extent. Based on the data the nanocomposite will be a suitable antibacterial material for incorporation in to polymers to be made as films to control the growth of microorganisms in areas such as food processing textiles and other health care domains. The antibacterial activity of nano composite was remarkable against *Staphylococcus aureus* where as it was less inhibitory towards *E. coli* and *S. typhi*. when tested.

From Table 1 it is evident that the antibacterial activity of the silver nanoparticles is in congruence with the SPR of the composites. The nanoparticles with SPR at the blue end have shown a better antibacterial activity than those with red SPR. The size of the silver nanoparticles showed a linear relationship with SPR and hence smaller particles with larger surface area were found to show better interaction with bacterial surface and thereby bactericidal effect.

Figure 6:
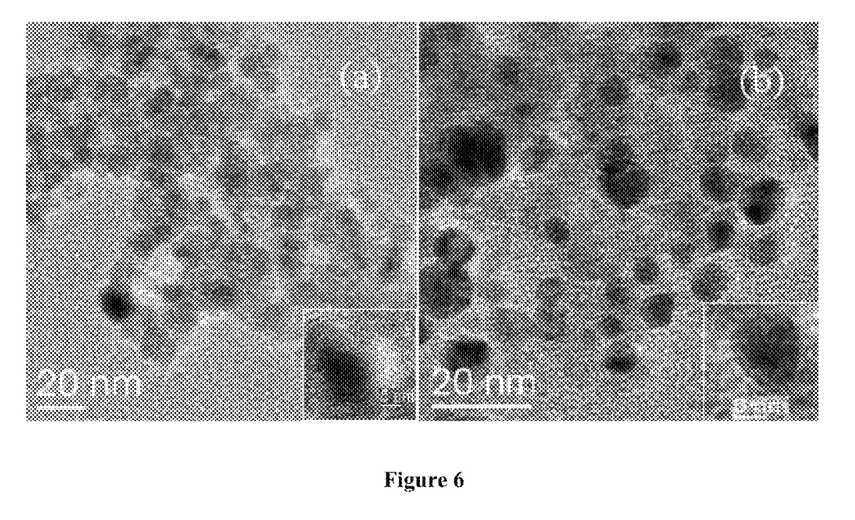
FIG. 6: TEM images of (a) and (b) γ-$Fe_2O_3$@Ag for (88.9% Fe+11.1% Ag). The inset shows these particles at higher magnification.
Figure 7:
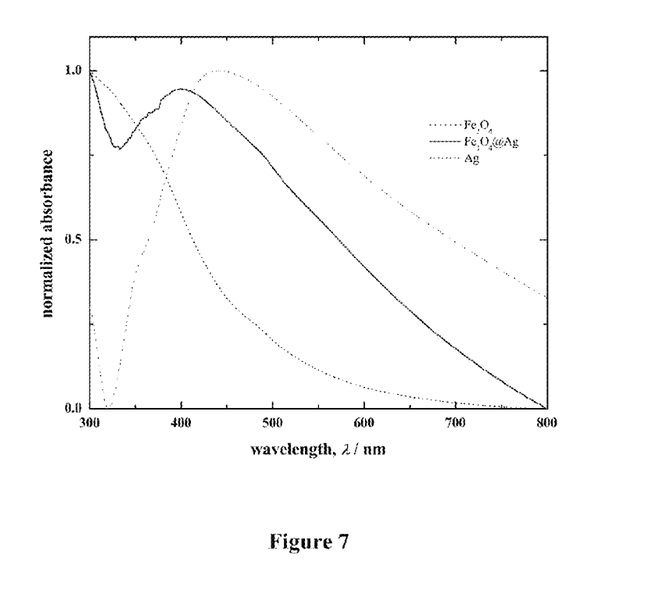
FIG. 7: UV-Vis absorption spectra of $Fe_3O_4$@Ag (solid lines), Ag sol (dash line) and $Fe_3O_4$ (dotted lines) nanoparticles, respectively.
Figure 8:
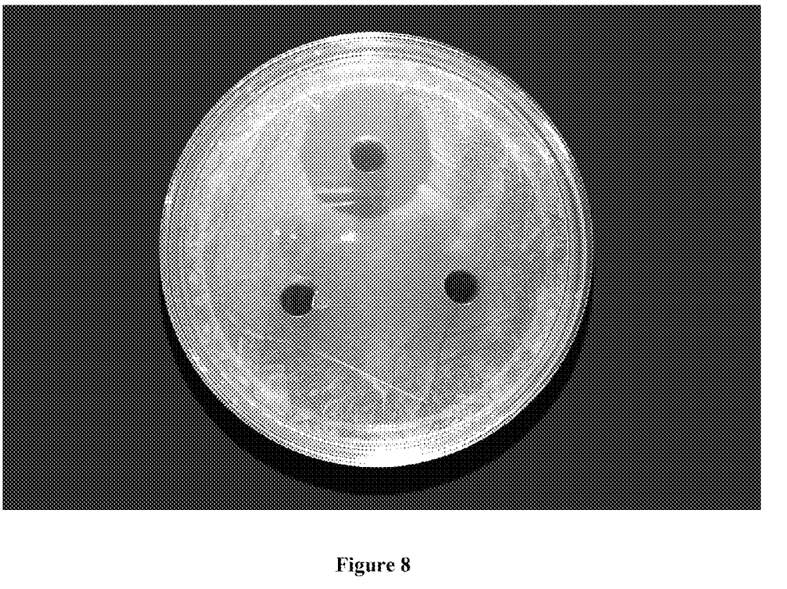
FIG. 8: Antibacterial inhibition of cellulose nano fiber and iron oxide embedded silver nano particle composite obtained by using hydrazine as the reducing agent.

Iron oxide embedded silver nanoparticles have the magnetic characteristics of iron oxide and the surface properties of silver nanoparticles. This is a major advantage, since separation of the particle under the influence of magnetic field is possible. Most of these nanoparticles when formed in a solution are capped by an organic layer and same is the case of the iron oxide nanoparticles as well as iron oxide embedded silver nano particles (see FIG. 6). These nanoparticles show their characteristic UV visible spectra as shown in FIG. 7. Due to the presence of a strong capping agent the surface effects of silver are not similar to pristine silver surface. In the case of nanocomposites of cellulose nano fibers and iron oxide embedded silver nanoparticles, the capping agent is the cellulose nano fibers itself. Since the cellulose fibers do not form a complete cover on silver surface, the silver surface behaves more like pristine silver surface. The cellulose nano fibers also releases the nanoparticles in a controlled fashion into the solution. This is true in the case of nanocomposites of cellulose nano fibers and silver nanoparticles. The antibacterial effects of composite of cellulose nano fiber with iron oxide embedded silver nanoparticle is shown in FIG. 8 and is comparable to the pure silver case shown in FIG. 4. The magnetic property of iron oxide embedded silver nanoparticle could be used to remove these nanoparticles from its environment, where it could probably have toxic effects of silver, by applying an external magnetic field.

Figure 9:
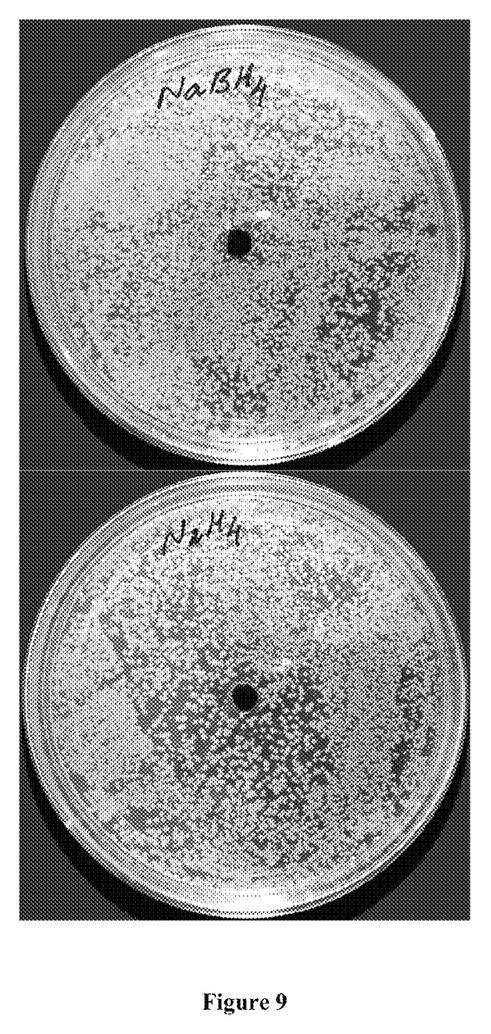
FIG. 9: Control antibacterial efficacy of bacterial cellulose nano fiber with sodium borohydride and hydrazine against *Staphylococcus aureus*. Both the experiments show no antimicrobial activity against the bacterium.

As a control experiment to show that the reducing agents like hydrazine and sodium borohydrate as well as the cellulose nano fibers do not show any antibacterial activity, we have tested the mixture of these in an antibacterial test culture and the results are displayed in FIG. 9. It is clear that these do not have any effect on the bacterial growth and their presence in the composite will not influence the observed results.

In conclusion a silver nanocomposite comprising of nanoparticulate bacterial cellulose and nanosilver was prepared in aqueous phase. The stabilization of the nanoparticles was achieved by the presence of water-dispersed cellulose particles in the reaction medium. The antibacterial activity had matched to a very larger extent with SPR. The optimal antibacterial activity was noticed in the composite which was prepared using hydrazine as reductant. The nanocomposite had inhibited the *S. aureus* during the growth process and bacterial cells in their stationery phase. The composite materials and the route of synthesis appear to be suitable for application in the preparation of antimicrobial food packaging films, water purification systems, medical dressings, inner textiles. Modifications need to be carried out to incorporate the nanocomposite into polymeric films for their optimum utilization. The utility of the material can be widened by exploring additional fictionalization.

TABLE 1

UV-visible absorption, pH and antibacterial characteristics of cellulose Ag composite obtained by using different reducing agents.

| reducing agent | Cellulose | pH | absorption peak (nm) | bacterial inhibition zone (radius in cm) |
|---|---|---|---|---|
| Hydrazine | As such | 8.2 | 415 | 2.0 |
| | NaOH treated | 8.2 | 397 | 2.6 |
| Sodium borohydride | As such | 9.8 | 401 | 1.0 |
| | NaOH treated | 9.9 | 401 | 1.4 |
| Hydroxylammonium hydrochloride | As such | 4.6 | 488 | 0 |
| | NaOH treated | 5.6 | 425 | 0 |
| Ethylene glycol | As such | 5.8 | 421 | 0 |
| | NaOH treated | 5.4 | 419 | 0 |
| Glucose | As such | 4.1 | 412 | 0 |
| | NaOH treated | 5.9 | 415 | 0 |
| Tri-sodium citrate | As such | 6.9 | 435 | 0 |
| | NaOH treated | 6.9 | 429 | 0 |

Experimental Section

Chemicals:

All the chemicals silver nitrate (Qualigens, 99.8%), hydroxonium hydroxide (Merck, 100%), sodium borohydride (Merck, ≥95%), hydroxyl ammonium hydrochloride (Merck, ≥98%), D-glucose (Qualigens, >99%), ethylene glycol (Laboratory Rasayan, >99%), tri-sodium citrate (x, ≥y %), sodium hydroxide (Merck, ≥97%) was used without further purification. Millipore water was used for all washing procedures as well as solutions preparation.

Silver Nanoparticles Loading on Cellulose Fibers:

In order to synthesize cellulose fibers silver nanocomposites we have used a range of reducing agents hydrazanium hydroxide, sodium borohydride, hydroxyl ammonium hydrochloride, tri-sodium citrate, D-glucose and ethylene glycol to reduce $Ag^+$ to silver nanoparticles. Weighed quantities of cellulose sample ~1% (w/w) is dispersed in 1 mM aqueous silver nitrate solution in a beaker and sonicated for half an hour. Aqueous solution of the reducing agents ~2-5 mM are added drop wise to the cellulose solution. The reactions are carried out at room temperature except in the case of sodium borohydride where ice-cold condition is maintained and in case of D-glucose, tri-sodium citrate and ethylene glycol, the solution is refluxed for an hour. In case of hydroxyl ammonium hydrochloride as reducing agent, 1 mM alkalinity is maintained by adding aqueous NaOH solution.

Silver Nanoparticles Loading on Cellulose Papers:

In order to load silver nanoparticles on cellulose papers, the paper is soaked in 1 mM aqueous silver nitrate solution for half an hour, washed with ethanol and water again soaked in 1 mM aqueous solutions of reducing agent (hydrazanium hydroxide or sodium borohydride) for half an hour. Finally they were washed with ethanol and water and dried in air at room temperature (~22° C.).

Measurements:

Uv-vis absorption measurements were done by using a Perkin-Elmer Lambda 900 UV/VIS/NIR spectrophotometer. Transmission electron microscopy (TEM) experiments were performed using JEOL 3010 with an operating voltage of 300 keV. Field Emission Scanning Electron Microscopy (FE-SEM) was done by using a Nova 600 NanoSEM (FEI, Germany). The composition mainly carbon, oxygen and silver of silver loaded cellulose were determined by using EDAX equipped to the FE-SEM. The pH measurements were done by using a Eutech $p^H$ 510. All the measurements were performed at room temperature (~22° C.).

Assay for Antibacterial Activity of Silver Nanocomposite:

The antibacterial activity of silver-cellulose nanocomposite was tested using *Staphylococcus aureus*. A fresh culture of the bacterium was prepared by inoculating a loop of inoculum into 50 ml of nutrient broth and BHI broth. The organism was monitored as 25% glycerol store in broth and was stored at 85° C. After incubating the culture at 37° C. for 15-20 hrs, serial dilution in the range $10^{-1}$-$10^3$ was made in 2 ml eppendorf tubes with sterile distilled water. Tryptic soy agar plates were prepared by adding 7.5 g of tryptic soy broth medium and 0.2 g of agar in 250 ml of distilled water. After autoclaving at 20 psi for 15 minutes the molter was pored into disposal petriplates at the rate of 15 ml/dish. After solidification of the medium under aseptic conditions 100 µl of $10^{-3}$ dilution *Staphylococcus aureus* culture was spread into each plate with a glass spreader. Wells were made with the help of a 7 mm cylindrical metal pipe. At the center of the well 50 µl of silver nanocomposite in solution form was placed. The petridishes were kept at 5° C.±2 in refrigerator for 2.0-2.5 hours. The plates were finally kept 37° C. for 20-24 hours in a BOD incubator. The zone and inhibition is reported as radius from the centre of the well under observation.

Preparation of $Fe_3O_4$ Core and Ag Shell Nanoparticles:

Materials:

All the chemicals $AgNO_3$ (Qualigens, 99.8%), $N_2H_5OH$ (Merck, ~100%), $FeCl_2.4H_2O$ (NP Chem), anhydrous $FeCl_3$ (Qualigens, 96.0%), HCl (Laboratory Rasayan, 35-38%), NaOH (Merck, 97%), $HNO_3$ (Laboratory Rasayan, 69-72%), 2-Napthalenethiol (Aldrich, 99%), Rhodamine 6G (SD fine chemicals, India, 95%) and Rhodamine B (SD fine chemicals, India, 80%) were used without further purification. Millipore water was used to make the solutions.

Synthesis:

The synthesis of $\gamma$-$Fe_2O_3$ nanoparticles is done following the procedures described in literature. In a typical synthetic method 25 ml. of aqueous solution containing 0.4 M $Fe^{2+}$, 0.8 M $Fe^{3+}$ and 0.4 M HCl is added drop wise to a moderately heated (~50° C.) 250 ml of aqueous 1.5 M NaOH solution under vigorous non-magnetic stirring. A black precipitate of $Fe_3O_4$ is formed immediately. After 15 minutes of stirring the precipitates are allowed to settle down, washed with water and magnetically separated. The precipitates are centrifuged at 6000 rpm and then washed twice with water and redispersed in 500 ml water.

By using hydrazanium hydroxide as reducing agent to coat Ag on $Fe_3O_4$. 2 ml (containing 0.12 mmol of Fe) of stock solution of $Fe_3O_4$ is dispersed in 8 ml of water. 1% aqueous solution of $AgNO_3$ is added to the solution to make appropriate concentration of $Ag^+$ in the solutions. Five set of concentrations, $10^{-4}$, $5\times10^{-4}$, $10^{-4}$, $5\times10^{-3}$ and $10^{-2}$ M each for $Ag^+$ was done. After 15 minutes 0.2 M aqueous solution of hydrazanium hydroxide is added drop wise with constant shaking. The final concentration of hydrazanium hydroxide is maintained two times higher than $Ag^+$. The solution turns to yellowish green for Ag. The particles are separated by using a magnet and washed 2-3 times with distilled water and finally they were dried under vacuum at room temperature for further characterization.

$Fe_3O_4$ Core and Silver Shell (Core-Shell) Nanoparticles Loading on Cellulose Fibers:

In order to synthesize cellulose fibers core-shell nanocomposites we have mixed the nanoparticles of $Fe_3O_4$ with cellulose fibers and reduced the silver on to the iron oxide nanoparticles as described in the earlier section.

Measurements:

Transmission electron microscopy (TEM) images were recorded by using JEOL 3010 with an operating voltage of 300 keV. Uv-Vis absorption measurements were done by using a Perkin-Elmer Lambda 900 UV/VIS/NIR spectrophotometer. The molar ratios of Fe to Ag were determined by EDAX measurements. Magnetization measurements were performed using a VSM in PPMS (Physical property measurement system) with magnetic fields up to 20 kOe at 298.15 K.

Assay for Antibacterial Activity of Silver Nanocomposite:

The antibacterial activity of core-shell-cellulose nanocomposite was tested using *Staphylococcus aureus*. A fresh culture of the bacterium was prepared by inoculating a loop of inoculum into 50 ml of nutrient broth and BHI broth. The organism was monitored as 25% glycerol store in broth and was stored at 85° C. After incubating the culture at 37° C. for 15-20 hrs, serial dilution in the range $10^{-1}$-$10^3$ was made in 2 ml eppendorf tubes with sterile distilled water. Tryptic soy agar plates were prepared by adding 7.5 g of tryptic soy broth medium and 0.2 g of agar in 250 ml of distilled water. After autoclaving at 20 psi for 15 minutes the molter was poured into disposal petriplates at the rate of 15 ml/dish. After solidification of the medium under aseptific conditions 100 µl of $10^{-3}$ dilution *Staphylococcus aureus* culture was spread into each plate with a glass spreader. Wells were made with the help of a 7 mm cylindrical metal pipe. At the center of the well 50 µl of silver nanocomposite in solution form was placed. The petridishes were kept at 5° C.±2 in refrigerator for 2.0-2.5 hours. The plates were finally kept 37° C. for 20-24 hours in a BOD incubator. The zone and inhibition is reported as radius from the centre of the well under observation.

I claim:

1. A nanoparticle composition consisting essentially of a plurality of cellulose nanofibers embedded with nanosized material selected from the group consisting of elemental silver and silver coated iron oxide and a combination thereof, wherein said nanoparticle composition is prepared by a process comprising the steps of:
   a) mixing a silver salt solution with the cellulose nanofibers to obtain a mixture; or adding a silver salt solution to an admixture of the cellulose nanofibers and iron oxide nanoparticles to obtain a mixture; or soaking the nanofibers in the form of cellulose paper in a silver salt solution; and
   b) adding a reducing agent to any of the mixtures obtained in step (a) to obtain said nanoparticle composition; or washing the soaked cellulose paper of step (a) followed by soaking the washed cellulose paper in a solution of reducing agent to obtain said nanoparticle composition, wherein the reducing agent is hydrazanium hydroxide or sodium borohydride, or a combination thereof, and wherein the nanoparticle composition has antibacterial activity against *Staphylococcus aureus*.

2. The nanoparticle composition as claimed in claim 1, wherein the iron oxide is selected from a group consisting of $Fe_3O_4$ and $\gamma\text{-}Fe_2O_3$.

3. The nanoparticle composition of claim 1, wherein the silver salt is selected from the group consisting of silver nitrate, silver chloride, silver carbonate, and any combination thereof.

4. The nanoparticle composition as claimed in claim 1, wherein the nanoparticle composition is used in the manufacture of an antibacterial medicament for an application selected from the group consisting of food packaging, clothing, medical application, face mask, laundry detergent, and air filter.

5. The nanoparticle composition as claimed in claim 1, wherein soaking the washed cellulose paper in a solution of reducing agent in step (b) is followed by steps of washing and drying the cellulose paper.

6. The nanoparticle composition as claimed in claim 1, wherein the nanosized elemental silver or nanosized silver coated iron oxide is uniformly embedded over cellulose fibers or cellulose paper; and wherein the nanoparticle composition is stable at least over a period of about 3 months.

\* \* \* \* \*